United States Patent [19]

Sims et al.

[11] Patent Number: 5,260,337
[45] Date of Patent: Nov. 9, 1993

[54] IBUPROFEN-MUSCLE RELAXANT COMBINATIONS

[75] Inventors: Robert T. Sims, Holicong; Thomas N. Gates, Doylestown; William Slivka, Philadelphia, all of Pa.

[73] Assignee: Merck & Co., Inc., Rahway, N.J.

[21] Appl. No.: 921,882

[22] Filed: Jul. 29, 1992

[51] Int. Cl.$^5$ ............... A61K 31/19; A61K 31/135
[52] U.S. Cl. ............................ 514/570; 514/646
[58] Field of Search ........................ 514/570, 646

[56] References Cited

U.S. PATENT DOCUMENTS

| | | | |
|---|---|---|---|
| 4,279,926 | 7/1981 | Bruzzese et al. | 424/316 |
| 4,851,444 | 7/1989 | Sunshine et al. | 514/570 |
| 4,877,620 | 10/1989 | Loew et al. | 424/451 |
| 4,923,898 | 5/1990 | Sunshine et al. | 514/557 |
| 4,980,375 | 12/1990 | Sunshine et al. | 514/570 |
| 4,994,604 | 2/1991 | Tung et al. | 562/401 |
| 5,009,895 | 4/1991 | Lui | 424/465 |

FOREIGN PATENT DOCUMENTS

| | | |
|---|---|---|
| 62-081311A | 4/1987 | Japan . |
| 2-191228 | 7/1990 | Japan . |
| 2197198A | 10/1987 | United Kingdom . |
| 2218633A | 5/1988 | United Kingdom . |

Primary Examiner—S. J. Friedman
Attorney, Agent, or Firm—Charles M. Caruso; Melvin Winokur; Carol S. Quagliato

[57] ABSTRACT

This invention relates to pharmaceutical compositions for use in the treatment of pain and inflammation and the treatment of muscle spasms and associated pain, soreness and tightness of muscles in mammalian organism, said composition comprising:

(i) an analgesically and anti-inflammatory effective amount of (S)-ibuprofen, or a salt thereof, substantially free of (R)-ibuprofen; and (ii) an amount effective in the treatment of muscle spasms of at least one of the muscle relaxants, or a therapeutically active stereoisomer thereof, substantially free of its other stereoisomers.

10 Claims, No Drawings

IBUPROFEN-MUSCLE RELAXANT COMBINATIONS

BACKGROUND OF THE INVENTION

The non-steroidal anti-inflammatory drugs (NSAID) have been utilized in the treatment of pain/inflammation and have been disclosed as useful in the treatment, management and mitigation of cold symptoms and the pain associated therewith.

Ibuprofen (2-(4-isobutylphenyl)propionic acid) is a well known and commonly employed NSAID. Recently, it has been found that a faster onset of pain relief and an enhanced analgesic response can be obtained by the utilization of the single enantiomer (S)-ibuprofen in comparison to racemic ibuprofen, (see for example U.S. Pat. No. 4,877,620).

Muscle relaxants are useful for the treatment of muscle spasms, and associated muscle pain, soreness and tightness, due to muscle strains, overexertion, and minor injuries of the back and neck. Both ibuprofen and muscle relaxants are also useful in relieving the symptoms associated with menstrual associated disorders, such as cramping.

Combinations of ibuprofen with muscle relaxants have been disclosed; however, despite the fact that the muscle spasm sufferer is in need of quick and enhanced relief there has been no consideration given to the employment of (S)-ibuprofen or a salt thereof, and more particularly a lysine or arginine salt thereof, in combination with a muscle relaxant for the treatment of pain and the relief of muscle spasm symptoms.

DETAILED DESCRIPTION OF THE INVENTION

This invention relates to pharmaceutical compositions for use in the treatment of pain and inflammation and the treatment of muscle spasms and associated muscle pain, soreness and tightness in a mammalian organism, said composition comprising:

(i) an analgesically and anti-inflammatory effective amount of (S)-ibuprofen, or a salt thereof, substantially free of (R)-ibuprofen; and (ii) an amount effective in the treatment of muscle spasms of at least one of the muscle relaxants, or a therapeutically active sterioisomer thereof, substantially free of its other stereoisomers.

This invention is also directed to a method of treating pain and inflammation and treating muscle spasm and associated symptoms in a mammalian organism in need of such treatment, comprising administering to such organism:

(i) an analgesically and anti-inflammatory effective amount of (S)-ibuprofen, or a salt thereof, substantially free of (R)-ibuprofen; and (ii) an amount effective in the treatment of muscle spasms of at least one of the muscle relaxants, or a therapeutically active sterioisomer thereof, substantially free of its other stereoisomers.

This invention is also directed to a method of eliciting an onset hastened and enhanced response for the treatment of pain and inflammation and the treatment of muscle spasm and associated symptoms in a mammalian organism in need of such treatment, comprising administering to such organism:

(i) an analgesically and anti-inflammatory effective amount of (S)-ibuprofen, or a salt thereof, substantially free of (R)-ibuprofen; and (ii) an amount effective in the treatment of muscle spasms of at least one of the muscle relaxants, or a therapeutically active sterioisomer thereof, substantially free of its other stereoisomers.

Substantially free of (R)-ibuprofen should be taken to mean that the ratio of (S)-ibuprofen to (R)-ibuprofen is at least 90:10. Substantially free with respect to a muscle relaxant stereoisomer should be taken to mean that the ratio of that stereoisomer to all other stereoisomers of the muscle relaxant is at least 90:10.

Salts of (S)-ibuprofen include pharmaceutically acceptable salts which include salts with alkali metals, such as sodium or potassium, salts with alkaline earth metals, such as calcium, or salts with other metals such as magnesium, aluminum, iron, zinc, copper, nickel or cobalt.

Pharmaceutically acceptable salts of (S)-ibuprofen further include the amino acid salts, particularly the basic amino acids such as lysine or arginine. Specifically included within the above composition is (S)-ibuprofen-(S)-lysine and (S)-ibuprofen-(R)-lysine.

The term mammal or mammalian organism includes but is not limited to man, dog, cat, horse and cow.

The term treatment encompasses the complete range of therapeutically positive effects associated with pharmaceutical medication including reduction of, alleviation of and relief from the symptoms or illness which affect the organism.

(S)-Ibuprofen may be prepared following the procedures disclosed in U.S. Pat. No. 4,877,620. Metal salts of ibuprofen may be obtained by contacting a hydroxide, or carbonate with ibuprofen. Amino acid salts of ibuprofen may be obtained by contacting an amino acid in solution with ibuprofen.

The pharmaceutical compositions of the present invention are useful in the treatment of pain and inflammation and the symptoms such as pain, soreness, tightness of muscles and skeletal-muscle spasms.

The utilization of (S)-ibuprofen in an analgesic/muscle relaxant combination offers significant advantages over the combination of racemic ibuprofen with a muscle relaxant.

(S)-Ibuprofen provides a faster onset of pain/inflammatory relief and an enhanced degree of relief compared to racemic ibuprofen. These benefits are increased in an (S)-ibuprofen/muscle relaxant combination as the muscle relaxant potentiates the action of (S)-ibuprofen.

Furthermore, the absence of (R)-ibuprofen provides significant benefits. The allergic contraindications sometimes associated with ibuprofen administration are absent or reduced in a composition wherein the (R)-ibuprofen is absent. Furthermore, the subject using the (S)-ibuprofen/muscle relaxant combination will no longer need to divert metabolic energy to the inversion of the (R)-enantiomer. Furthermore, the absence of (R)-ibuprofen in an (S)-ibuprofen/muscle relaxant combination is particularly advantageous as a lesser metabolic burden is placed on the urogenital system for the excretion of the (R)-enantiomer or its metabolites. The absence of inversion reduces or eliminates the formation and incorporation into fatty tissue of hybrid-ibuprofen containing triglycerides. The renal burden and renal toxicities sometimes associated with ibuprofen therapy are reduced or absent in a substantially (R)-ibuprofen free composition.

Where only a single stereoisomer of the muscle relaxant is active (therapeutically active stereoisomer), the absence of the inactive substances in the present composition avoids undesirable toxic interactions and clearly avoids the metabolism necessary to remove the nonactive entity.

The absence of inactive enantiomers, particularly (R)-ibuprofen provides for significant size and weight advantages in a combination dosage form, particularly a sustained release dosage form. Where a sustained release dosage of ibuprofen may have required 800 to 1000 mg, the employment of (S)-ibuprofen reduces the weight to 400 to 500 mg, and provides for a more practical size tablet for an ibuprofen/muscle relaxant combination.

An effective amount of (S)-ibuprofen, or a salt thereof, for use in an unit dose composition of this invention may range from 50 to 800 mg (S)-ibuprofen. The preferred amount of (S)-ibuprofen is about 100 to 400 mg. The amount of a salt such as (S)-ibuprofen-(S)-lysine is determined based on the amount of (S)-ibuprofen contained therein.

The muscle relaxant employed herein may be selected from either of the polysynaptic depressant type or the non-polysynaptic depressant type. The polysynaptic depressant type of muscle relaxant exerts a selective action on the polysynaptic neuronal systems that control muscle tone, probably blocking or retarding the transmission of nervous impulses in internuncial pathways with the spinal cord and at higher levels. The polysynaptic depressant type of muscle relaxant or compounds with muscle relaxant activity include but are not limited to: carisoprodol, chlorzoxazone, cyclobenzaprine, dantrolene, diazepam, metaxalone, baclofen, quinine, orphenadrine and methocarbanol.

The non-polysynaptic depressant type of muscle relaxant includes compounds that act as depressants of muscle-spindle activity and compounds that act on α-motoneurons.

The pharmaceutically acceptable salt of the muscle relaxant may be employed in the instant invention. Such pharmaceutically acceptable salts include citrate, hydrochloride, sodium, sulfate and the like.

The preferred muscle relaxant is cyclobenzaprine hydrochloride.

Included within this invention are any diastereomers and/or enantiomers of the muscle relaxant. Where a particular therapeutically active stereoisomer is not commercially available it may be prepared following standard resolution chemistry from the available racemic mixture.

The amount of the muscle relaxant useful in the practice of the present invention may vary from about 1 mg to 750 mg depending on the specific muscle relaxant. The preferred amount of muscle relaxant is selected from a range 1 to 25 mg per tablet.

The present compositions may be administered in the form of tablets, caplets, gelcaps, capsules, elixirs, syrups or a suspension. For oral administration the active components may be admixed with a pharmaceutically acceptable diluent such as lactose, starch, sucrose, cellulose, magnesium stearate, dicalcium phosphate, calcium sulfate, mannitol and in a liquid composition, ethyl alcohol. Acceptable binders such as PVP, starch, gelatin, natural sugars, corn sweeteners, natural and synthetic gums such as acacia, sodium alginate, carboxymethylcellulose, polyethylene glycol and waxes, may also be admixed with the active components. Where necessary lubricants such as magnesium stearic acid talc, boric acid, sodium benzoate, sodium acetate and sodium chloride, and disintegrators such as starch, methylcellulose, agar, bentonite and guar gum and super disintegrators such as docusate sodium, sodium starch glycollate or cross-linked PVP may also be included.

The active components may also be formulated in sustained release formulations. These formulations may be employed in oral, dermal, rectal or vaginal administrations. Such sustained release forms also include layered formulations which provide for distinct release ratio and thus may be more beneficial in allowing for short and long term relief.

The following examples illustrate the compositions of the present invention and as such are not to be considered as limiting the invention set forth in the claims appended hereto.

| EXAMPLE I | |
|---|---|
| (S)-ibuprofen, Muscle Relaxant Tablet | |
| (S)-ibuprofen-(S)-lysine | 342 mg |
| Cyclobenzaprine hydrochloride | 5 mg |
| PVP | 15 mg |
| Avicel PH101 | 40 mg |
| Magnesium Stearate | 4 mg |
| EXAMPLE 2 | |
| (S)-ibuprofen, Muscle Relaxant Tablet | |
| (S)-ibuprofen-(S)-lysine | 342 mg |
| Cyclobenzaprine hydrochloride | 2.5 mg |
| PVP | 15 mg |
| Avicel PH101 | 40 mg |
| Magnesium Stearate | 4 mg |
| EXAMPLE 3 | |
| (S)-ibuprofen, Muscle Relaxant Sustained Release | |
| (S)-ibuprofen | 400 mg |
| Cyclobenzaprine hydrochloride | 5 mg |
| PVP | 30 mg |
| Avicel PH101 | 80 mg |
| Magnesium Stearate | 8 mg |
| Methocel E10MCR | 66 mg |
| Methocel K100MLV | 200 mg |
| EXAMPLE 4 | |
| (S)-ibuprofen-(S)-lysine/Muscle Relaxant Solution | |
| (S)-ibuprofen-(S)-lysine | 342 mg |
| Cyclobenzaprine hydrochloride | 5 mg |
| q.s. syrup | 5 ml |

What is claimed is:

1. A pharmaceutical composition for use in the treatment of pain and inflammation and the treatment of muscle spasms and associated pain, soreness and tightness of muscles in a mammalian organism and adapted for unit dosage oral administration, said composition comprising:
   (i) an analgesically and anti-inflammatory effective amount of (S)-ibuprofen, or a salt thereof, substantially free of (R)-ibuprofen; and
   (ii) an amount effective in the treatment of muscle spasms, and associated symptoms, of a muscle relaxant selected from the group consisting of cyclobenzaprine, chlorzoxanzone, methocarbamol and the pharmaceutically acceptable salts thereof, or a therapeutically active stereoisomer thereof, substantially free of its other stereoisomers.

2. The composition of claim 1 where the ibuprofen is present as the salt (S)-ibuprofen-(S)-lysine, or (S)-ibuprofen-(R)-lysine.

3. The composition of claim 1 comprising at least 50 mg of (S)-ibuprofen.

4. The composition of claim 1 wherein the muscle relaxant is cyclobenzaprine hydrochloride.

5. The composition of claim 1 wherein the muscle relaxant is selected from cyclobenzaprine hydrochloride and chlorzoxanzone.

6. A method of treating pain and inflammation and treating muscle spasms and associated pain, soreness and tightness of muscles in a mammalian organism in need of such treatment, comprising administering to such organism:

(i) an analgesically and anti-inflammatory effective amount of (S)-ibuprofen, or a salt thereof, substantially free of (R)-ibuprofen;

(ii) an amount effective in the treatment of muscle spasms, and associated symptoms, of a muscle relaxant selected from the group consisting of cyclobenzaprine, chlorozoxanzone, methocarbamol and the pharmaceutically acceptable salts thereof, or a therapeutically active stereoisomer thereof, substantially free of its other stereoisomers.

7. A method of eliciting an onset hastened and enhanced response for the treatment of pain and inflammation and the treatment of muscle spasms and associated pain, soreness and tightness of muscles in a mammalian organism in need of such treatment, comprising administering to such organism (i) an analgesically and anti-inflammatory effective amount of (S)-ibuprofen, or a salt thereof, substantially free of (R)-ibuprofen; and (ii) an amount effective in the treatment of muscle spasms, and associated symptoms, of a muscle relaxant selected from the group consisting of cyclobenzaprine, chlorzoxanzone, methocarbamol and the pharmaceutically acceptable salts thereof, or a therapeutically active stereoisomer thereof, substantially free of its other stereoisomers.

8. A method of reducing the side effects associated with the administration of an ibuprofen/muscle relaxant combination which comprises the administration of (S)-ibuprofen, or a salt thereof, substantially free of (R)-ibuprofen, and a muscle relaxant selected from the group consisting of cyclobenzaprine, chlorzoxanzone, methocarbamol and the pharmaceutically acceptable salts thereof, or a therapeutically active stereoisomer thereof substantially free of its other stereoisomers.

9. The method of claim 6 wherein the muscle relaxant is selected from cyclobenzaprine hydrochloride and chlorzoxanzone.

10. The method of claim 6 wherein the muscle relaxant is cyclobenzaprine hydrochloride.

* * * * *